(12) United States Patent
Evans

(10) Patent No.: US 6,226,546 B1
(45) Date of Patent: May 1, 2001

(54) CATHETER LOCALIZATION SYSTEM AND METHOD FOR PERFORMING MEDICAL DIAGNOSTICS

(75) Inventor: Richard John Evans, Winchester (GB)

(73) Assignee: Roke Manor Research Limited, Hampshire (GB)

( * ) Notice: Subject to any disclaimer, the term of this patent is extended or adjusted under 35 U.S.C. 154(b) by 0 days.

(21) Appl. No.: 09/159,457

(22) Filed: Sep. 24, 1998

(30) Foreign Application Priority Data

Sep. 24, 1997 (GB) ................................................ 9720176

(51) Int. Cl.$^7$ ........................................................ A61B 5/05
(52) U.S. Cl. ........................ 600/424; 600/437; 600/443; 600/448; 600/463; 600/466; 607/115; 607/116; 606/130; 128/899
(58) Field of Search ..................... 600/437, 443, 600/448, 450, 463, 466, 461, 459, 471, 417; 607/115, 116; 606/130; 128/898, 899, 916

(56) References Cited

U.S. PATENT DOCUMENTS

| | | | |
|---|---|---|---|
| 5,797,396 | * 8/1998 | Geiser et al. ........................ | 382/128 |
| 5,797,849 | * 8/1998 | Vesely et al. ........................ | 600/461 |
| 5,817,022 | * 10/1998 | Vesely ................................. | 600/443 |
| 5,924,990 | * 7/1999 | Nachtomy et al. .................. | 600/443 |

* cited by examiner

Primary Examiner—Marvin M. Lateef
Assistant Examiner—Jeoyuh Lin
(74) Attorney, Agent, or Firm—Evenson, McKeown, Edwards & Lenahan, P.L.L.C.

(57) ABSTRACT

A catheter localization system for generating information appertaining to a three dimensional map of a part of a human or animal body from which three dimensional map a position of said catheter may be determined. The catheter localization system includes a catheter having a catheter head which is arranged in use to be conveyed through the human or animal body to a desired localization, a plurality of acoustic transducers disposed about said catheter head at predetermined localizations and a signal processing unit which operates to determine said three dimensional map of said part of a human or animal body consequent upon signals received by a plurality of acoustic transducers acting as acoustic receivers, which acoustic signals were generated by at least one of said plurality of acoustic transducers acting as an acoustic source.

17 Claims, 4 Drawing Sheets

CATHETER LOCALIZATION SYSTEM AND METHOD FOR PERFORMING MEDICAL DIAGNOSTICS

Figure 1:
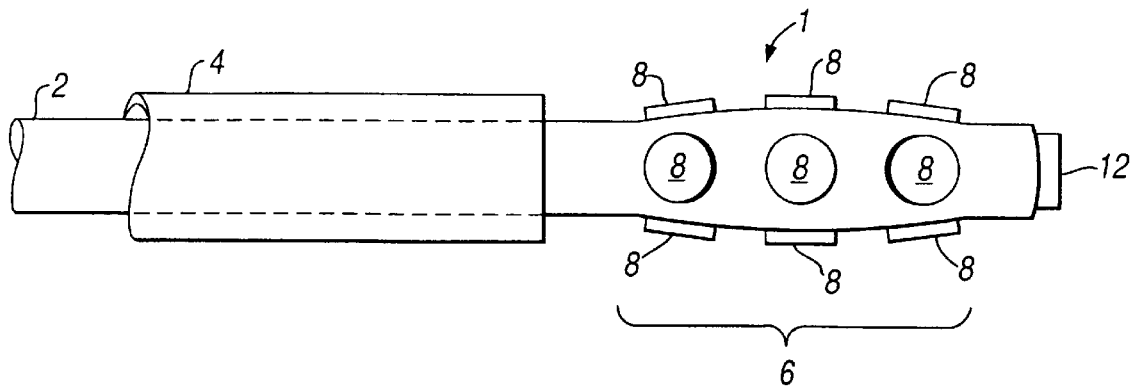

The present invention relates to catheter localization systems which serve to provide data appertaining to a position of a tip of a catheter with reference to a part of the human or animal body.

Catheters provide a means for accessing a remotely located part of the human or animal body via a vein or artery so as to provide a means to perform medical diagnostics or treatment of that part of the body. For example, a catheter may be provided with a sensor disposed on a tip of the catheter which may further comprise an elongated flexible member arranged to move axially within an outer sheath. The tip including the electric sensor is arranged to pass through a vein or artery of the body using the outer sheath and arranged to be positioned at or near the heart so as to provide signals representative of the electrical activity of the heart. In such operations it is an important requirement to be able to determine a position of the catheter head so as to provide correct interpretation of the diagnostic information and correct positioning of the catheter during treatment. A process of determining a position of the catheter head with reference to a three-dimensional image of a part of the body is known as localization.

Electrocardiography is a process for recording electrical signals created by a heart using electrodes applied externally and more particularly electrodes positioned on tips of catheters inserted within the heart. In known endocardial catheter technology, great use is made of in-theatre fluoroscopy to locate and guide catheters to positions within the heart where measurements are required. The use of fluoroscopy has a disadvantage in that inevitably theatre staff and patients are exposed to X-ray radiation.

A further disadvantage with known techniques for catheter localization, is a requirement for correction to be made for the effect of patient movement including movement of the heart caused by its pumping action and movement caused by breathing. In these known systems this movement associated with pumping of the heart and breathing are overcome by relating the measurements taken by the catheter to a particular phase of the heartbeat, and measuring the position of the primary catheter relative to a point or points on a reference catheter. It is this reference catheter that is inserted into the body under the guidance of X-ray fluoroscopy and positioned throughout the procedure in a convenient and anatomically well defined position such as the coronary sinus. The reference catheter serves to provide, to a certain level, some compensation for the movement caused by the patient's breathing and the beat of the heart. This is effected since the movement of both reference and primary catheters will be substantially the same for both catheters. However, use of a reference catheter has a disadvantage in that this requires surgical introduction in addition to the primary catheter which, as an invasive procedure, carries some inconvenience and risk. Furthermore, repositioning of the reference catheter relative to the heart is subject to variability in that it will be difficult to reproduce the same position of the reference catheter in a subsequent introduction of the reference and the primary catheters.

The aforementioned disadvantages represent a technical problem which is addressed by the catheter localization system according to the present invention.

According to the present invention there is catheter localization system for determining a position of a head of a catheter with reference to a part of the human or animal body from mapping information appertaining to a three-dimensional map of said body, said catheter localization system comprising a plurality of acoustic transducers disposed about said catheter head in spaced apart relationship, which catheter head in use is positioned at a predetermined location in said body part, and a signal processing unit which operates to determine said three dimensional map of said body part consequent upon a first set of measurement data appertaining to measured times of flight of acoustic signals generated by at least one of said plurality of acoustic transducers acting as an acoustic signal source and received by said plurality of acoustic transducers acting as acoustic receivers, said times of flight of said acoustic signals being representative of a distance travelled between said source acoustic transducer and said receiver acoustic transducers reflected from said body part.

By arranging for the catheter head to be populated with acoustic transducers, measurements made of distances travelled by acoustic signals from an acoustic transducer acting as a source of the acoustic signals to acoustic transducers acting as acoustic receivers provide information appertaining to a three dimensional representation of the part of the human or animal body in which the catheter is disposed.

Advantageously the catheter head may be moved to at least one other predetermined location, and at least one other set of measurement data generated. The other set of measurement data is representative of a plurality of distance measurements generated from measured times of flight of acoustic signals between at least one of said plurality of acoustic sensors acting as an acoustic signal source, reflected via said part of the body. The signal processing unit may thereafter operate to determine the three dimensional map of said part of the body by matching said first and said other sets of measurement data.

The operation of matching the first and other sets of measurement data may be effected by an image processing algorithm such as an elastic networks algorithm The measurement data detected by the acoustic transducers acting as receivers may be used by a signal processing unit to determine the location of the acoustic transducers on the catheter head with reference to a reference acoustic transducer.

The signal processing unit may operate to determine the mapping data representative of a three dimensional image of the part of the human body and secondly determine the location of the catheter head with reference to the measurement data in combination with the map of the part of the body.

The catheter tracking system may further include a display means which serves to display said mapping data representative of a three dimensional image of the body part and wherein said catheter head is also displayed.

According to a first aspect of the present invention there is provided a method of determining a position of a catheter head within a part of the human or animal body comprising the steps of
- generating acoustic signals from at least one of a plurality of acoustic transducers acting as an acoustic signal source, disposed on said catheter head,
- receiving said acoustic signals with said plurality of acoustic transducers acting as acoustic receivers after said acoustic signals have been reflected from a wall of the body part,
- determining a first set of measurement data appertaining to distances travelled by said acoustic signals from said at least one acoustic transducer acting as an acoustic signal source to said plurality of acoustic transducers acting as acoustic receivers and determining mapping data representative of a three dimensional map of the part of the human or animal body.

Figure 2:
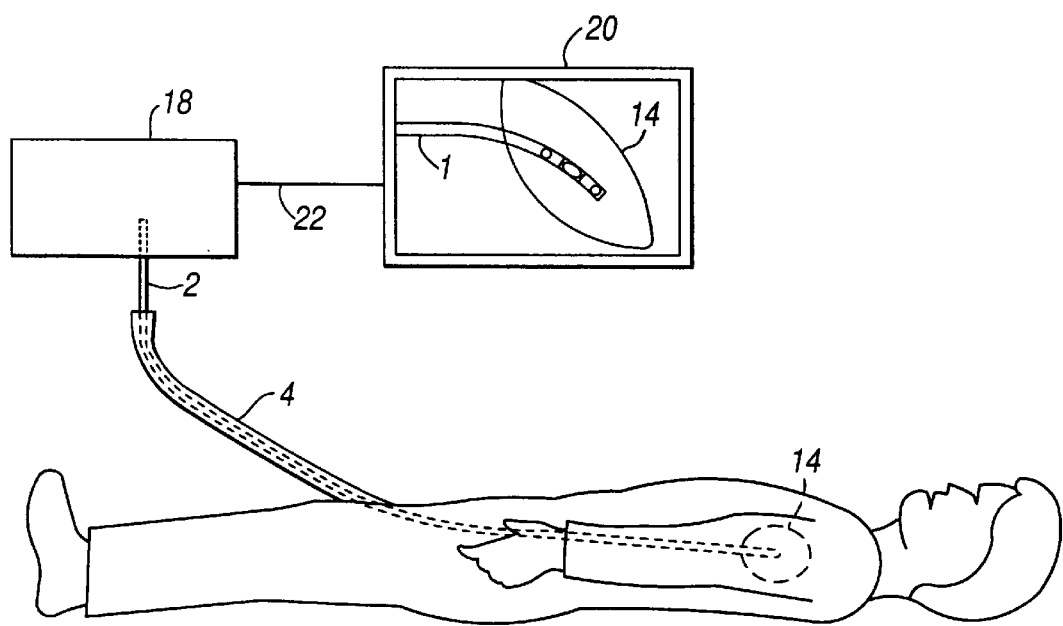
Figure 3:
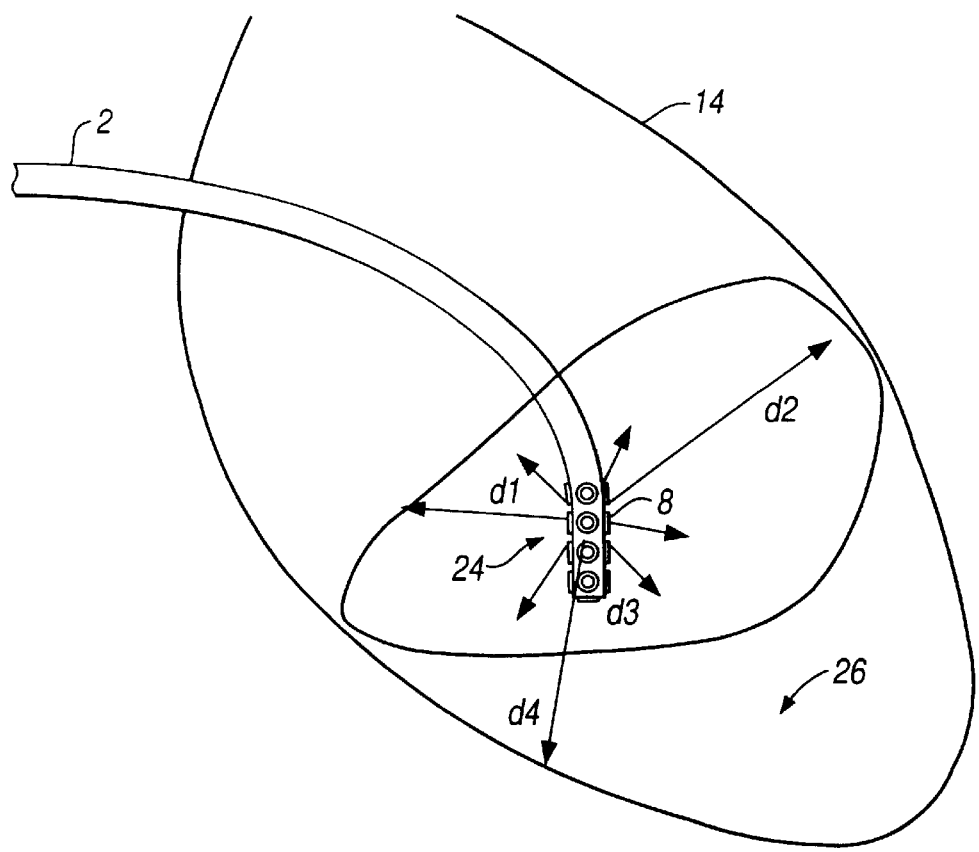
Figure 4:
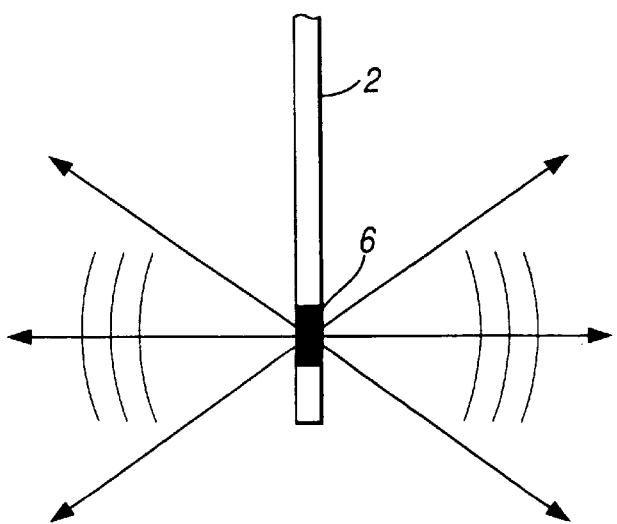
Figure 5:
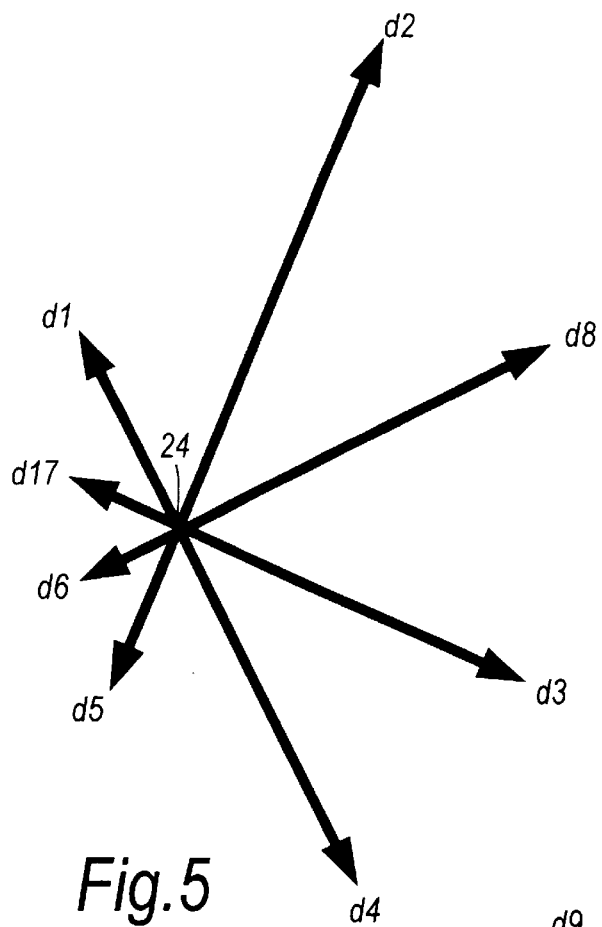
Figure 6:
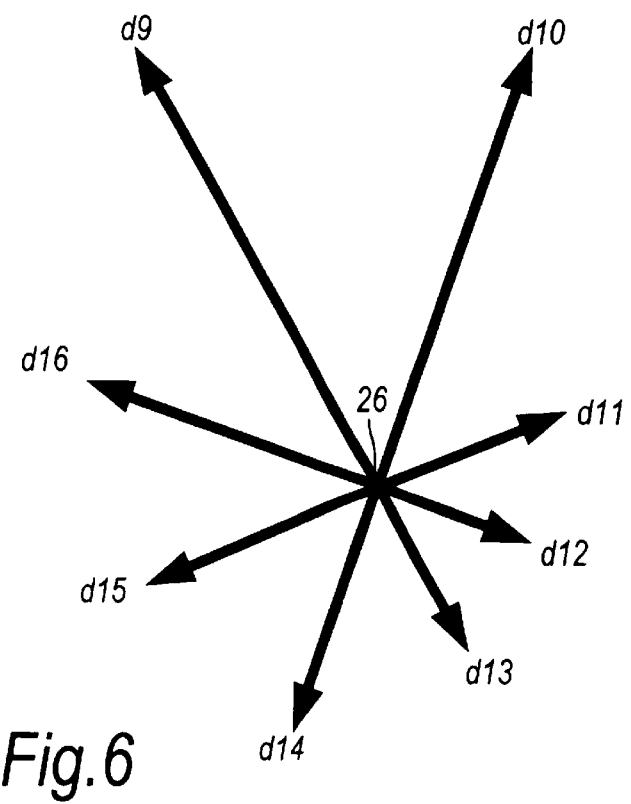
Figure 7:
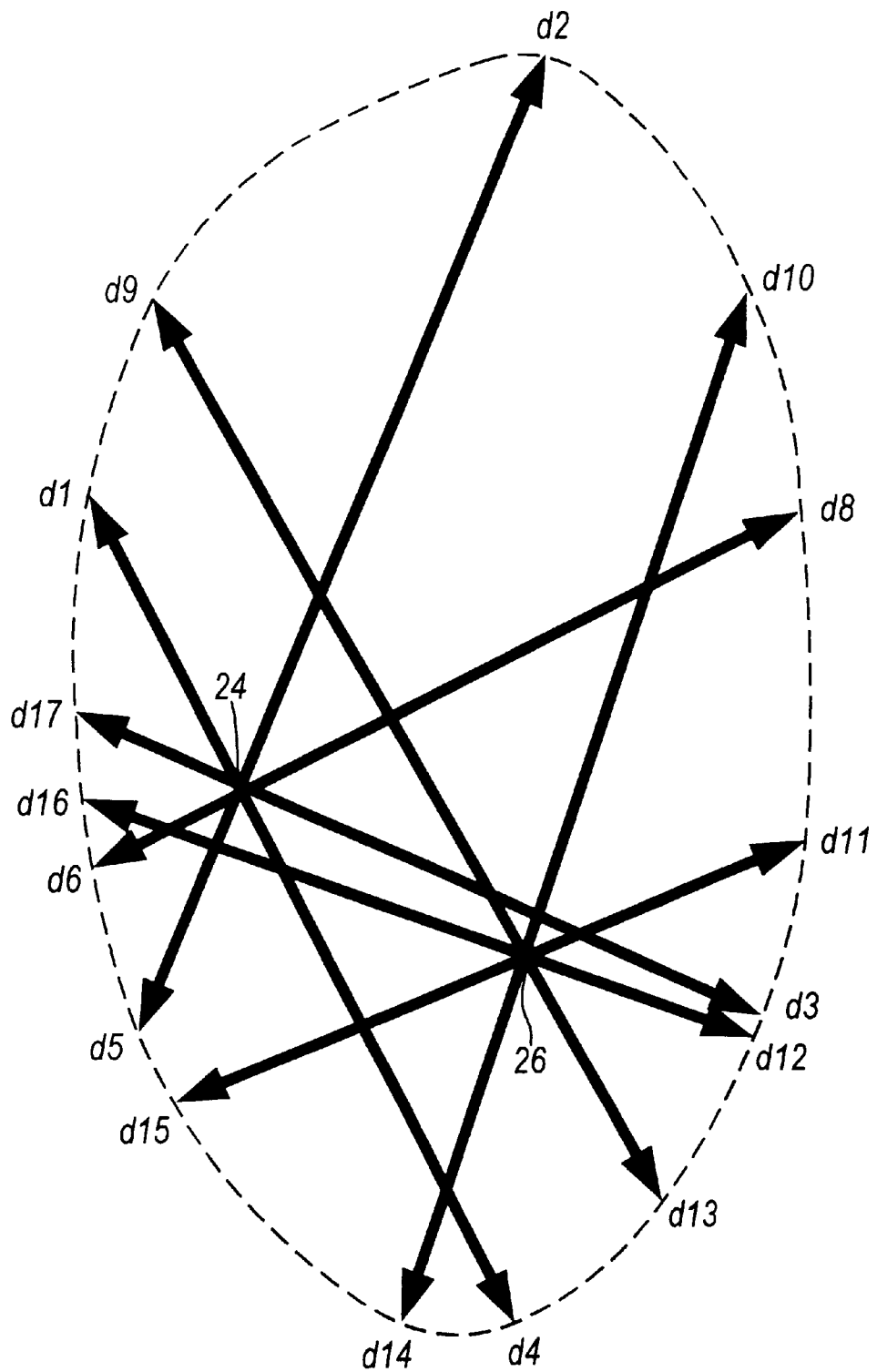

One embodiment of the present invention will now be described by way of example only with reference to the accompanying drawings wherein:

FIG. 1 is a schematic diagram of a catheter head for use with a catheter localization system, FIG. 2 shows the catheter localization system in use in determining a position of a catheter head within the heart of a human body, FIG. 3 is a schematic diagram illustrating an operation of the catheter localization system, FIG. 4 is a schematic representation of the generation of acoustic signals from the catheter head shown in FIG. 1, FIG. 5 is a diagram representing the generation of acoustic signals at a first predetermined position shown, FIG. 6 is a diagram representing the generation of acoustic signals at a further predetermined position shown, and FIG. 7 is a diagram representing a combination of FIGS. 5 and 6.

FIG. 1 provides a schematic illustration of a catheter which forms part of a catheter localization system in accordance with one embodiment of the present invention. In FIG. 1 a catheter 1, is shown to be comprised of an inner elongated member 2, and an outer sheath 4. The catheter 1, further comprises generally a head 6, upon which are disposed acoustic transducers 8 in spaced apart relationship. For example the acoustic transducers could be Pezo electric devices. The elongated member 2, is arranged to move co-axially within the sheath 4. An arrangement wherein the catheter shown in FIG. 1 is used to perform an electrocardiograph is shown in FIG. 2 where parts also appearing in FIG. 1 bear identical numerical designations.

An electrocardiography is a process for recording electrical signals created by a heart using electrodes applied externally and more particularly electrodes positioned on a tip of the catheter inserted into the heart. Thus, in the present embodiment, the tool 12, is representative of an electrical sensor which in use must be arranged to be positioned at a desired localization within the human heart. To this end, the catheter 1, is introduced into the body via a main artery and manoeuvred along the main artery to a location juxtaposition the heart of the patient. By operation of signals generated by the acoustic transducers 8, acting as a source of acoustic signals and received by acoustic transducers 8, acting as a receiver of acoustic signals a signal processing unit 18, serves to generate a three dimensional representation of the inside of the heart which may be displayed on a display means or monitor 20, coupled to the,signal processing unit via a conductor 22.

In operation the catheter localization system, serves to generate the three dimensional representation of the heart in accordance with the following process described with reference to FIGS. 3 and 4, which shows the catheter 1, within the heart in more detail and FIG. 4 which illustrates the emission of an acoustic signal. In both FIGS. 3 and 4 parts also appearing in FIGS. 1 and 2 bear identical numerical designations. Mapping data appertaining to a three dimensional representation of the heart is generated from measured distances between the catheter head 6, and the wall of the heart. These distances are measured by determining the time of flight of acoustic signals from an acoustic signal source to an acoustic sensor. Thus, by measuring the time of flight of acoustic signals from the acoustic signal sources to the acoustic sensors, a distance may be determined for each acoustic signal generated by an acoustic transducer 8, acting as an acoustic signal source and detected by acoustic transducers acting as sensors. Therefore, for each acoustic transducer 8, an acoustic signal is generated and the time of flight of acoustic signals from the acoustic transducer 8, via the heart wall, is used to determine a distance in a plane and angle corresponding to the position of the acoustic transducer 8. Thus, by positioning the acoustic transducers about the head of the catheter 2, a plurality of distances from the head 6, of the catheter 1 may be determined. This is illustrated in FIG. 3 by the distances D1, D2, D3 and D4, which are shown to be positioned adjacent arrows representative of the direction of flight of the acoustic signals. As will be readily appreciated by those skilled in the art, although the example embodiment of the present invention has been described with acoustic transducers operating in different modes, first as a signal source, and then as an acoustic sensor, separate acoustic sources and sensors could be used and sited at different locations about the catheter head.

An embodiment of the present invention could be effected with any number of acoustic transducers. The more transducers there are disposed on the catheter head, the greater the degree of resolution provided by distance measurements generated by these transducers. For example with sixty four transducers uniformly distributed about the catheter head will provide distance measurements separated by only twenty five degrees. Use of sixty four beams have been reported in a publication entitled 'Arteries Scanned by World's Smallest Camera', by J. Newell published on the Britania Internet Magazine, 1996 (http://www.britania.com/science/scanners. html). However there is a practical limitation on the number of electrical connections which can be made to the catheter at an opposite end to the catheter head. Hence a smaller number of transducers would be preferred. A workable system can be based on sixteen elements, which would provide measurement acoustic beams with an angular separation of forty five degrees.

As will be seen from FIG. 1, the acoustic transducers 8, are disposed in a spaced apart relationship and arranged to be positioned at angles on a blistered surface of the elongated member 2 in the vicinity of the catheter head 6, so that acoustic signals generated thereby may be directed at angles arranged to provide measurements in a general approximation to a hemispherical form. Thus each of the acoustic transducers 8, are arranged to generate signals and measure the time of flight of signals which return from the heart wall and, in accordance with the time of flight, measure the distance in a direction determined by the shape and position of the acoustic transducers on the elongated member 2. An example technique which may be used to determine the mapping data representative of the three dimensional image of the heart will now be described with reference to FIGS. 4, 5, 6 and 7.

FIG. 4 provides an illustrative representation of acoustic signals generated by the acoustic transducers disposed on the catheter head 6, wherein the angle of the transducers provides vector measurements of distances in accordance with the direction of travel of the acoustic signals. Thus, with the catheter head 6, disposed within the heart 14, a first set of distance measurements may be generated. An example of such a first set is shown in FIG. 5. In FIG. 5 the catheter head 6, is positioned within the heart wall at a position 24. Position 24 is also shown as an illustration in FIG. 3. At position 24 the signal processing unit 18, operates to energise the acoustic transducers and to generate acoustic signals which travel from the acoustic transducers to the heart wall and return to the acoustic transducers. The time of flight of the acoustic signals therefore serves to determine the distances D1, D2, D3, D4, D5, D6, D7 and D8. However, this may not be sufficient to determine a three dimensional map of the heart wall. Therefore, the catheter head may be repositioned at a position 26. This is also shown in FIG. 3. In position 26, the measurement process is repeated and distances D9, D10, D11, D12, D13, D14, D15 and D16 are generated by the acoustic transducers in combination with the signal processing unit 18. This is represented by the diagram shown in FIG. 6. The signal processing unit 18, thereafter operates to superimpose the distance measurements determined at points 24 and 26 and using an image processing and interpolation technique to determine the three dimensional map of the heart wall 14. This is shown conceptually in FIG. 7 where the distances measured from points 24 and 26 in FIGS. 5 and 6 are shown to be superimposed and resolved so that an inside surface of the heart wall is resolved in a from of a three dimensional.

As will be readily appreciated mapping a three dimensional structure in accordance with a plurality of measurements of distances from a point within that structure may be effected in a number of ways. Suitable image processing techniques may be used to effect the resolution of the distance measurements provided at different points. Examples of such image processing techniques which would be appropriate are:

(i) Least squares fitting methods using parametric shape model, an illustration of which is provided in a publication entitled 'Multivariate Analysis', by K. V. Mardia, J. T. Kent, J. M. Bibby, published by Academic Press 1979.

(ii) Methods based on point distribution models, an illustration of which is provided in a publication entitled 'Training Models of Shape from Sets of Examples', by T. F. Cootes, C. J. Taylor et al, proceedings of the British Machine Vision Conference 1992, Ed. D. Hogg, R. Boyle, published by Springer Verlag 1992.

(iii) Methods used on so called elastic networks, active contour models or snakes, an illustration of which is provided in a publication entitled 'Snakes: Active Contour Models', by M. Kass, A. Witkin, D. Terzopoulos, published in Proceedings of the First International Conference on Computer Vision, published by the Computer Society Press of IEEE, 1987.

As an example of an image processing method which serves to form the three-dimensional image, the elastic networks technique will be described in more detail. This is an iterative process where nodes of a net are initialised and provided with arbitrary positions in, for example, a best fit sphere. Thereafter each node behaves according to a dynamic mechanical model in which it is subject to two types of forces. These are;

a) forces resulting from a nodes position relative to its immediate neighbours in the net (normally these are based on spring-like models of tension and stiffness) and, b) forces resulting from measurements of shape to be fitted.

If predetermined positions at which the distance measurements were taken arc known, then the nodes would be attracted towards the measured positions of the heart wall. However, it is unlikely that the elastic networks method can be extended to the situation where a position of the catheter head at the point of measurement is not known. This can be done by providing an approximate initial estimate of a position of the catheter head at which the measurements were taken and then iteratively adjusting a solution to the network of nodes according to the three dimensional map.

Once the three dimensional map of the inside of the heart has been established, the position of the catheter head at any position within the heart may be determined by regenerating distance measurements from each of the acoustic transducers and, with reference to the inside of the heart wall determined by the three dimensional map, resolving a position of the catheter head. Thus the process steps used to determine a position of the catheter head within the heart are as follows:

Step 1

The catheter is introduced into the heart in accordance with normal procedure.

Step 2

An initial set of distance measurements are established in accordance with a time of flight of acoustic signals generated and received by the acoustic transducers. A position of the catheter head at this point defines an initial coordinate system.

Step 3

A further set of distance measurements are established in accordance with a time of flight of acoustic signals at a different position within the heart chamber.

Step 4

The measurement data at each of these positions is processed to form a reference data appertaining to a three dimensional representation of the inside of the heart.

Step 5

A new set of distance measurements are taken in accordance with the time of flight of acoustic signals from a current position of the catheter head, and from these distance measurements a location of the catheter head is determined with respect to the three dimensional map of the heart wall.

As will be appreciated by those skilled in the art, various modifications may be made to the embodiment hereinbefore described without departing from the scope of the present invention. In particular, operation of the acoustic localization technique may be effected by separate acoustic signal generators and acoustic sensors. Furthermore, the acoustic transducers or acoustic signals and sensors may be disposed at a plurality of sites on the elongated member 2, such that a three dimensional map of the heart wall may be established contemporaneously from signals generated from the acoustic transducers or signal generators at the different sites on the elongated member 2. Furthermore, the process of generating measurement data may be made substantially continuously such that image processing algorithms operate continuously to resolve a three dimensional image from measurements taken as the catheter moves through the body. As such, a surgeon or clinician will not be required to initiate any functions to generate the three dimensional map of the heart wall and, furthermore, the operation of thereafter determining the location of the catheter head may be effected automatically.

The catheter head may furthermore be provided with a tool 12, which may be used to determine an electrocardiograph. Alternatively, the tool 12, may be another type of sensor or may be used to effect some surgical operation on the inside of the heart.

What is claimed is:

1. A system for determining a position of a head of a catheter with reference to a body part of a human or animal body from mapping information appertaining to a three-dimensional map of said body, said system comprising a first plurality of acoustic transducers disposed about said catheter head in spaced apart relationship, which catheter head in use is positionable at a predetermined location in said body part, and a signal processing unit which operates to determine said three dimensional map of said body part, based upon a first set of measurement data appertaining to measured times of flight of acoustic signals generated by at least one of said first plurality of acoustic transducers acting as an acoustic signal source and received by said first plurality of acoustic transducers acting as acoustic receivers, said times of flight of said acoustic signals being representative of a distance traveled between said acoustic signal source and said acoustic receivers reflected from said body part.

2. The system as claimed in claim 1, wherein:
said catheter head is movable to at least one other predetermined location, for generating at least a second set of measurement data, representative of a plurality of distance measurements generated from measured times of flight of acoustic signals between at least one of said plurality of acoustic sensors acting as an acoustic signal source, and reflected via said body part; and
said signal processing unit determines said three dimensional map of said body part by matching said first and second sets of measurement data.

3. The system as claimed in claim 2, wherein said signal processing unit further operates to determine a location of the acoustic transducers on the catheter head with reference to a reference acoustic transducer from at least one of said first and said at least a second set of measurement data.

4. The system as claimed in claim 2, wherein said matching of said first and said at least a second set of measurement data is effected by at least one of an elastic networks, least squares fitting and point distribution modeling image processing algorithm.

5. The system as claimed in claim 2, wherein the signal processing unit further operates to determine a location of the catheter head with reference to at least one of the first and second sets of measurement data in combination with the map of the part of the body.

6. A catheter localization system as claimed in claim 2, said catheter head further comprising at least one other plurality of acoustic transducers disposed at a predetermined location on said catheter head, which at least one other plurality of acoustic transducers operates to generate at least one other set of measurement data, said other set of measurement data being representative of a plurality of distance measurements generated from measured times of flight of acoustic signals between at least one of said plurality of acoustic sensors acting as an acoustic signal source, reflected via said part of the body, and said signal processing unit operates to determine said three dimensional map of said part of the body by matching said first and said other sets of measurement data.

7. The system as claimed in claim 1, wherein:
said catheter head further comprises at least a second plurality of acoustic transducers disposed at predetermined locations on said catheter head, for generating at least a second set of measurement data representative of a plurality of distance measurements generated from measured times of flight of acoustic signals between at least one of said second plurality of acoustic sensors acting as an acoustic signal source, and reflected via said body part; and
said signal processing unit determines said three dimensional map of said body part by matching said first and second sets of measurement data.

8. The system as claimed in claim 7, wherein said signal processing unit further operates to determine a location of the acoustic transducers on the catheter head with reference to a reference acoustic transducer from at least one of said first and said at least a second set of measurement data.

9. The system as claimed in claim 7, wherein said matching of said first and said at least a second set of measurement data is effected by at least one of an elastic networks, least squares fitting and point distribution modeling image processing algorithm.

10. The system as claimed in claim 7, wherein the signal processing unit further operates to determine a location of the catheter head with reference to at least one of the first and second sets of measurement data in combination with the map of the part of the body.

11. The system as claimed in claim 1, further comprising a display unit which displays said mapping data representative of a three dimensional image of said part of the human or animal body and said catheter.

12. The system as claimed in claim 1, wherein said catheter head further includes a substantially blistered raised volume upon which said acoustic transducers are disposed, said raised volume providing an angular displacement of acoustic signals generated by said acoustic transducers.

13. A method of determining a position of a catheter head within a part of a human or animal body comprising the steps of
generating acoustic signals from at least one of a plurality of acoustic transducers acting as an acoustic signal source, disposed on said catheter head,
receiving said acoustic signals with said plurality of acoustic transducers acting as acoustic receivers after said acoustic signals have been reflected from a wall of the body part,
determining a first set of measurement data appertaining to distances traveled by said acoustic signals from said at least one acoustic transducer acting as an acoustic signal sources to said plurality of acoustic transducers acting as acoustic receivers, and
determining mapping data representative of a three dimensional map of the part of the human or animal body.

14. The method as claimed in claim 13, further include the steps of
generating at least a second set of measurement data appertaining to distances traveled by said acoustic signals from said at least one acoustic transducer to said plurality of acoustic transducers, which at least a second set of measurement data is determined at a different location within said body part, and
matching said first said and said at least a second set of measurement data so as to facilitate generation of said three dimensional map.

15. The method as claimed in claim 14, wherein the step of matching said first set and said at least a second set of measurement data includes use of an elastic network, least squares fitting or point distribution model image processing algorithm.

16. A method of determining a position of a catheter head as claimed in claim 15, further including the step of determining a location of the catheter head with reference to at least one of the first and the other sets of measurement data in combination with the map of the part of the body.

17. The method as claimed in claim 10, further including the step of
determining a location of the catheter head with reference to at least one of the first and a second set of measurement data in combination with the map of the part of the body.

* * * * *